United States Patent [19]

Tsuruoka et al.

[11] Patent Number: 4,469,643
[45] Date of Patent: Sep. 4, 1984

[54] PHOSPHORUS-CONTAINING COMPOUNDS AND PROCESS FOR PRODUCING THE SAME

[75] Inventors: Takashi Tsuruoka, Kawasaki; Satoshi Imai, Yokohama; Atsuyuki Satoh, Yokohama; Tetsuro Watanabe, Yokohama; Koji Watanabe, Machida; Shigeharu Inouye; Taro Niida, both of Yokohama, all of Japan

[73] Assignee: Meiji Seika Kaisha Ltd., Tokyo, Japan

[21] Appl. No.: 550,750

[22] Filed: Nov. 10, 1983

Related U.S. Application Data

[62] Division of Ser. No. 388,209, Jun. 14, 1982.

[30] Foreign Application Priority Data

Jun. 30, 1981 [JP] Japan .................... 56-100566
Feb. 26, 1982 [JP] Japan .................... 57-28925

[51] Int. Cl.³ .............. C07F 9/48; A61K 31/13; A61K 31/66
[52] U.S. Cl. .............. 260/502.5 G; 260/502.4 R; 424/211
[58] Field of Search .............. 260/502.5 G, 502.4 R

[56] References Cited

U.S. PATENT DOCUMENTS 2,648,695  8/1953  Smith ............... 260/502.4 R
4,147,780  4/1979  Dingwall et al. ..... 260/502.5 G
4,168,963  9/1979  Rupp et al. ......... 260/502.5 G
4,264,532  4/1981  Tsuruoka et al. .... 260/502.5 G Primary Examiner—J. E. Evans
Attorney, Agent, or Firm—Frishauf, Holtz, Goodman & Woodward

[57] ABSTRACT

Disclosed are compounds having the following general formula:

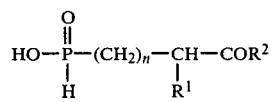

wherein n is an integer of 1 or 2; $R^1$ is an amino group when n is 2, or an amino group or a hydroxyl group when n is 1; and $R^2$ is a hydroxyl group when n is 1, or a hydroxyl group or a group of the formula

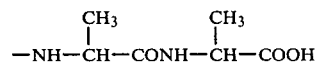

when n is 2;

and microbiological process for producing the same. The compounds are useful as precursors for raising the production rate of SF-1293 substance. Some of the compounds are also useful as intermediates for synthesis of 2-amino-4-(hydroxy)(methyl)phosphinoylbutyric acid and the SF-1293 substance.

5 Claims, 4 Drawing Figures

PHOSPHORUS-CONTAINING COMPOUNDS AND PROCESS FOR PRODUCING THE SAME

This is a division of application Ser. No. 388,209, filed June 14, 1982.

This invention relates to novel phosphorus-containing compounds and process for producing the same.

More particularly, this invention relates to novel compounds 2-amino-4-(hydroxy)phosphinoylbutyric acid (hereinafter referred to as MP-101 substance), 2-amino-4-(hydroxy)phosphinoylbutyryl-L-alanyl-L-alanine (hereinafter referred to as MP-102 substance), 2-amino-3-(hydroxy)phosphinoylpropionic acid (hereinafter referred to as MP-103 substance, and 2-hydroxy-3-(hydroxy)phosphinoylpropionic acid (hereinafter referred to as MP-104 substance) represented by the general formula mentioned later; and microbiological process for producing the same by cultivating microorganisms which produce the MP-101, MP-102, MP-103 and MP-104 substances under aerobic conditions and recovering these substances from the culture broth.

The present inventors have studied on the improved process for the production of a useful herbicide SF-1293 substance (which is disclosed in Japanese Patent Publication No. 639/1976 and U.S. Pat. No. 3,832,394) and, during the studies, found that the SF-1293 substance-producing microorganism *Streptomyces hygroscopicus* SF-1293 strain produces the MP-101 and MP-102 substances in its culture broth to which no cobalt was added, and that these substances are identified to be 2-amino-4-(hydroxy)phosphinoylbutyric acid and a tripeptide containing said phosphorus-containing amino acid, i.e., 2-amino-4-(hydroxy)phosphinoylbutyryl-L-alanyl-L-alanine, respectively based on physicochemical properties described herein later; and further that a mutant of said SF-1293 substance-producing microorganism *Streptomyces hygroscopicus* SF-1293 strain produces the MP-103 and MP-104 substances in a large amount, and that these substances are identified to be 2-amino-3-(hydroxy)phosphinoylpropionic acid and 2-hydroxy-3-(hydroxy)-phosphinoylpropionic acid, respectively; and in addition, that the production of SF-1293 substance may be increased by addition of these substances at the stage of cultivations of the SF-1293 substance-producing SF-1293 strains. This invention has been thus accomplished.

According to this invention there is provided novel phosphorus-containing compounds (MP-101, MP-102, MP-103 and MP-104 substances) represented by the following general formula:

wherein n is an integer of 1 or 2; $R^1$ is an amino group when n is 2, or an amino group or a hydroxyl group when n is 1; and $R^2$ is a hydroxyl group when n is 1, or a hydroxyl group or a group of the formula when n is 2; and process for producing MP-101, MP-102, MP-103 and MP-104 substances, which comprises cultivating a MP-101, MP-102, MP-103 and MP-104 substances-producing microorganism under aerobic conditions and recovering MP-101, MP-102, MP-103 and/or MP-104 substances from the culture broth.

Any microorganisms of the genus Streptomyces may be used in this invention so long as they produce MP-101, MP-102, MP-103 and MP-104 substances in sufficient amount to recover them from the culture broth. As for the production of MP-101 and MP-102 substances, such strains of the genus Streptomyces may be exemplified by the aforesaid *Streptomyces hygroscopicus* SF-1293 strain (FERM No. 996; ATCC No. 21705; International Deposit FERM BP-130, under Budapest Treaty, dated May 1, 1981), whose morphological characteristics are fully described in the aforesaid Japanese Patent Publication No. 639/1976 and U.S. Patent No. 3,832,394). As for the production of MP-103 and MP-104 substances, the strains of the genus Streptomyces may be exemplified by the aforesaid mutant of *Streptomyces hygroscopicus* SF-1293 strain. This strain has been named as *Streptomyces hygroscopicus* MP-103 and deposited in the Fermentation Research Institute, Agency of Industrial Science and Technology, Ministry of International Trade and Industry (Japan) (FERM No. 6328; International Deposit FERM BP-131, under Budapest Treaty, dated February 8, 1982), whose morphological characteristics are identical with those of the parent *Streptomyces hygroscopicus* SF-1293 strain except for smaller bearing of spores.

As is often observed with other strains of the genus Streptomyces, the characteristics of the strains SF-1293 and MP-103 tend to be variable and they readily undergo mutation as the result of artificial mutation such as irradiation by ultraviolet ray or X-ray, or treatment with chemicals. Any mutants to be obtained through such mutations may be used in this invention if they are strains of the genus Streptomyces, capable of producing MP-101, MP-102, MP-103 and MP-104 substances.

In the production process of this invention, strain SF-1293 or MP-103 is cultivated in a culture medium containing conventional nutrients assimilable by microorganisms. For the nutrient source, those commercially used for cultivation of microorganisms of the genus Streptomyces may be used. For instance, as the carbon source, there may be mentioned glucose, starch, glycerin, sucrose, hydrolyzed starch and molasses. They may be used either solely or in combination. As the nitrogen source, there may be mentioned soybean meal, wheat malt, meat extract, peptone, dry yeast, corn steep liquor, ammonium sulfate, sodium nitrate and the like, which may be used either solely or in combination. Further, when necessary, inorganic salts such as calcium carbonate, sodium chloride, potassium chloride and phosphates may be added. Furthermore, organic or inorganic substances may be added suitably to promote the growth of the microorganism and the production of MP-101, MP-102, MP-103 and MP-104 substances.

The cultivation is performed by a liquid culture, in particular and most preferably, by a submerged culture, under aerobic conditions. Temperature suitable for the cultivation ranges from 25° to 35° C. and in most instances it is around 28° C. The cultivation is performed suitably for 3 to 7 days and more suitably for 4 to 6 days.

In the case of MP-101 and MP-102 substances, MP-102 substance is first produced and accumulated in the culture broth after 3 to 6 days cultivation in a liquid medium. When the cultivation is performed over a longer period of time, then the alanyl-alanine moiety of MP- 102 substance is hydrolyzed to afford MP-101 substance as a result of the conversion reaction. The maximum production of MP-101 substance is achieved after 8 to 11 days of cultivation, when almost no MP-102 substance is present in the culture broth. Accordingly, in order to perform purification of MP-101 and MP-102 substances, the cultivation is stopped when the production in culture broth of the both substances reaches the maximum (usually 5 to 6 days for MP-102 substance and 8 to 9 days for MP-101 substance), then the substances are extracted and isolated from the culture broth, whereby the purification may be performed most effectively.

For the purification and isolation of MP-101, MP-102, MP-103 and MP-104 substances from the filtrate of culture broth, any methods of separation and purification employed for isolation of metabolic products of microorganisms from culture broth may be used. More concretely, since MP-101, MP-102, MP-103 and MP-104 substances are amphoteric or acidic water-soluble substances, they may be purified by using a cation-exchange resin such as Amberlite IR-120 (available from Rohm & Haas Co.) and Dowex 50W (available from Dow Chemical Co.), or an anion-exchange resin such as Amberlite IRA-400 (available from Rohm & Haas Co.) and Dowex 1×2 (available from Dow Chemical Co.), or by chromatography with Sephadex (available from Pharmacia Co.), cellulose, silica gel or charcoal.

Such purification may be performed preferably be combining the above-mentioned techniques. For instance, a method of passing through Dowex 50W (H+ form) resin column to eliminate basic impurities is a suitable purification method.

Physicochemical properties of MP-101, MP-102, MP-103 and MP-104 substances obtained by the process of the invention are given below:

MP-101 substance

Figure 1:
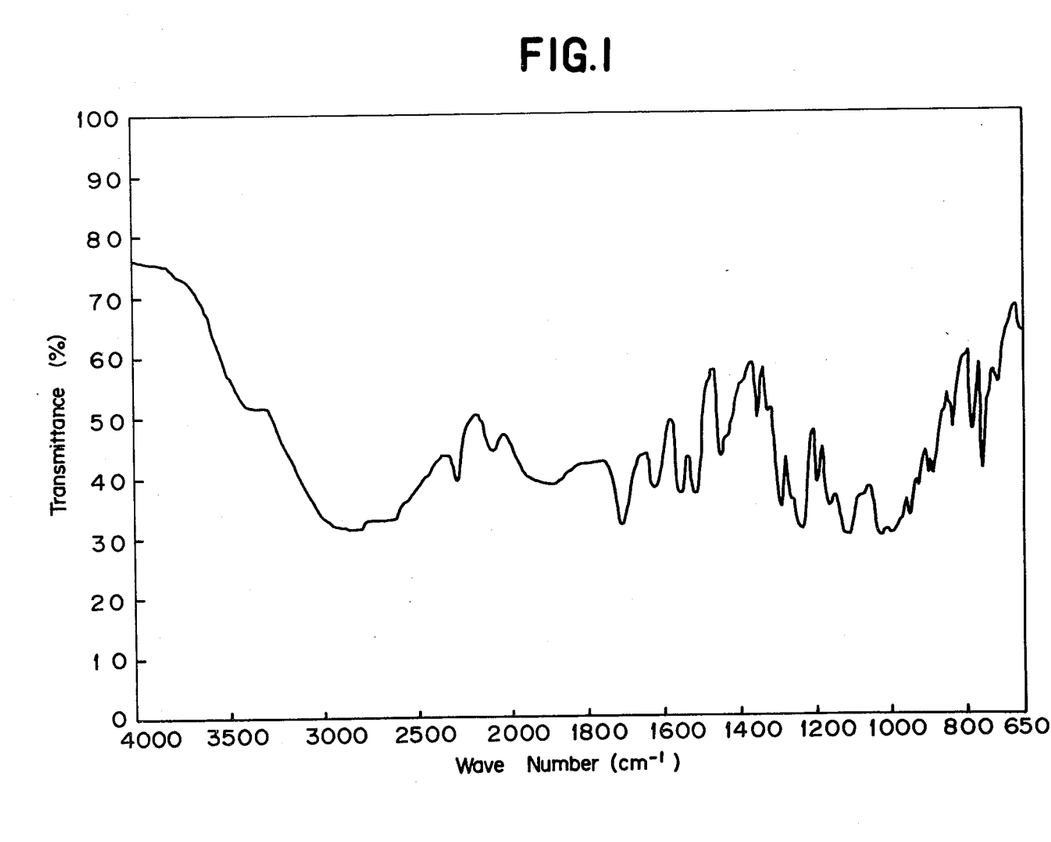

Appearance: White crystals.
Melting point: 221° to 222° C. with decomposition.
Solubility: Readily soluble in water, hardly soluble in organic solvents such as ethanol, acetone, ethyl acetate, chloroform and benzene.
Specific rotation: $[\alpha]_D^{20} = +28.9°$ (c 1, 1N hydrochloric acid)
Ultraviolet absorption spectrum: Terminal absorption only.
Infrared absorption spectrum: (As shown in FIG. 1) Characteristic absorption bands at 2500~3000, 1710, 1620, 1550, 1518, 1240, 1110, 1020, 850, 780 cm$^{-1}$ (KBr disc method).
Elementary analysis: C, 28.96; H, 6.06; N, 8.21; O, 37.90; P, 18.23%.
FD-mass spectrum: m/e: 168 (M+1)
Color reaction: Possitive for ninhydrin, potassium permanganate; Negative for molish, anthrone.
Silica gel thin layer chromatography: Rf=0.18 (n-butanol:acetic acid:water=2:1:1)
Cellulose thin layer chromatography: Rf=0.49 (ditto)

From the elementary analysis and FD-mass spectrum given above, MP-101 substance is determined to have the molecular formula $C_4H_{10}NO_4P$ (molecular weight: 167).

From the physicochemical properties described above, as well as other studies, MP-101 substance is indentified to be L-2-amino-4-(hydroxy)phosphinoylbutyric acid having the following formula (I):

MP-102 substance

Figure 2:
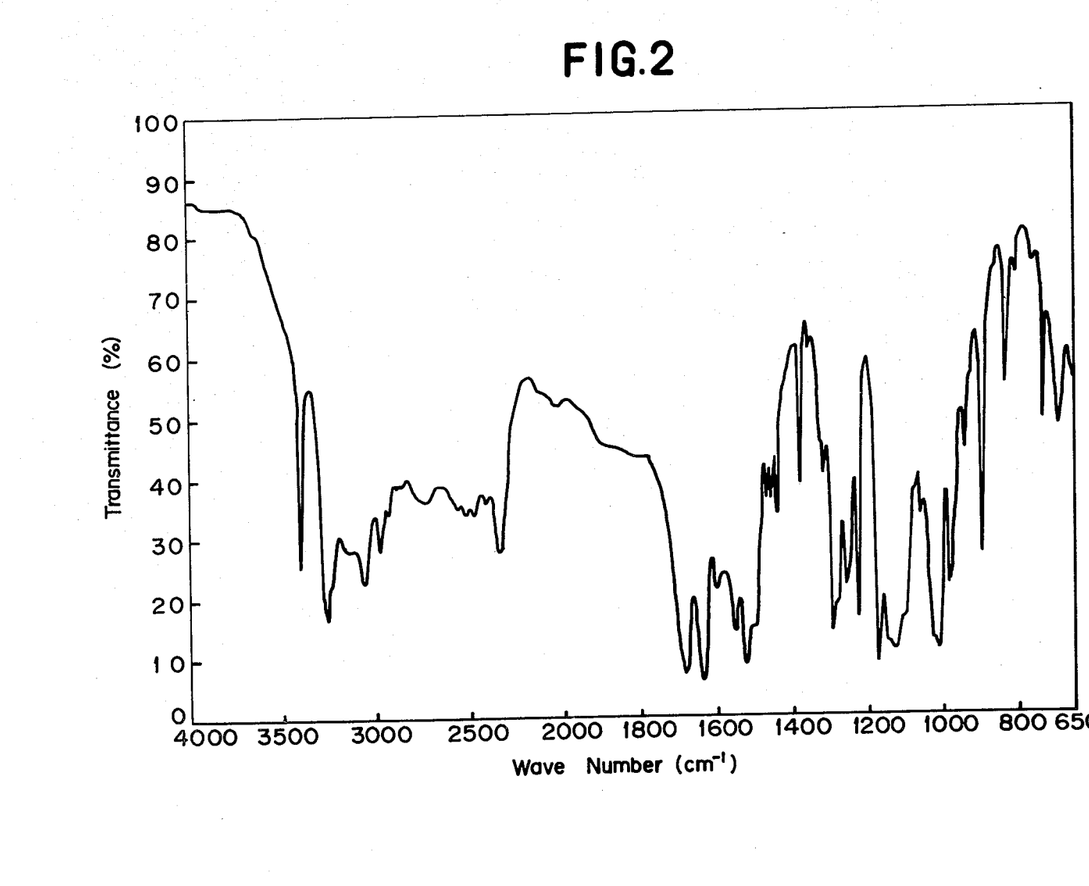

Appearance: White crystals.
Melting point: 226° to 228° C. with decomposition.
Solubility: Readily soluble in water, hardly soluble in organic solvents such as ethanol, acetone, chloroform, ethyl acetate and benzene.
Specific rotation: $[\alpha]_D^{21} = -37.7°$ (c 1, 1N hydrochloric acid)
Ultraviolet absorption spectrum: Terminal absorption only.
Infrared absorption spectrum: (As shown in FIG. 2) Characteristic absorption bands at 3400, 3260, 1685, 1640, 1520, 1295, 1130, 1010, 900, 850 cm$^{-1}$ (KBr disc method)
Elementary analysis: C, 39.02; H, 6.62; N, 12.98; O, 31.17; P, 9.73%.
FD-mass spectrum: m/e: 310 (M+1)
Color reaction: Positive for ninhydrin and potassium permanganate; Negative for anthrone.
Silica gel thin layer chromatography: Rf=0.25 (n-butanol:acetic acid:water=2:1:1)
Cellulose thin layer chromatography: Rf=0.67 (ditto)

From the elementary analysis and FD-mass spectrum given above, MP-102 substance is determined to have the molecular formula $C_{10}H_{20}N_3O_6P$ (molecular weight: 309).

Hydrolysis of MP-102 substance with 6N hydrochloric acid at 110° C. for 20 hours yields one mole of MP-101 substance and two moles of L-alanine.

From the physicochemical properties described above, as well as other studies, MP-102 substance is identified to be L-2-amino-4-(hydroxy)phosphinoylbutyryl-L-alanyl-L-alanine of the following formula (II):

MP-103 substance

Figure 3:
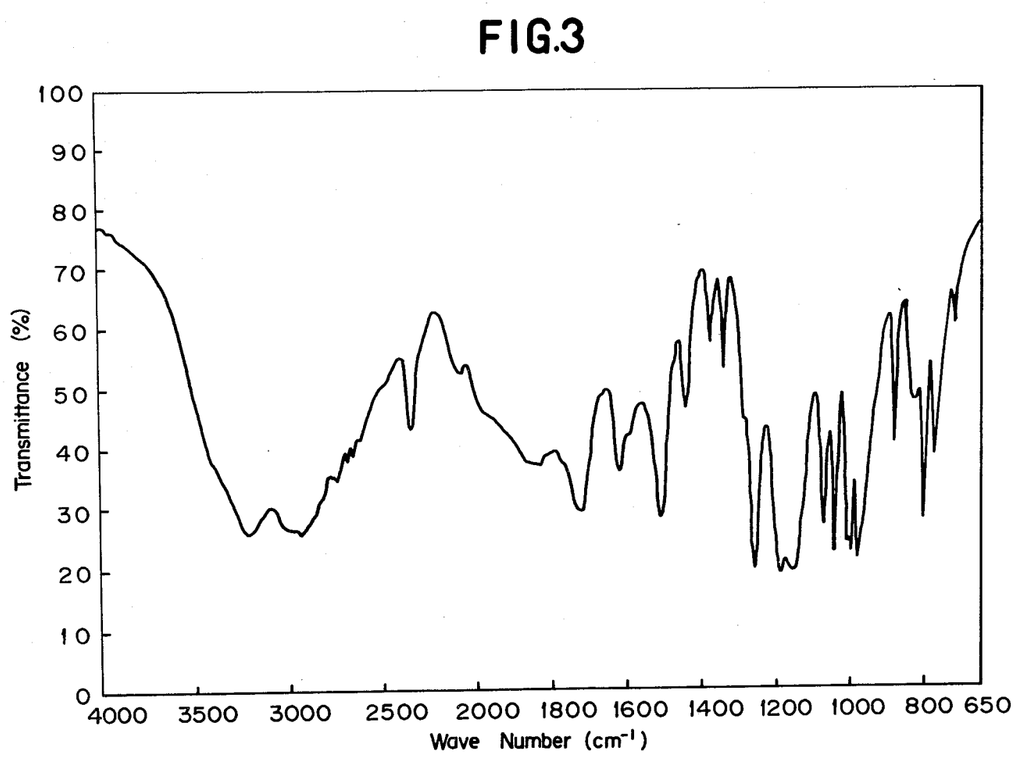

Appearance: White crystals.
Melting point: 196°~197° C. with decomposition.
Solubility: Readily soluble in water, hardly soluble in organic solvents such as ethanol, acetone, ethyl acetate and ethyl ether.
Specific rotation: $[\alpha]_D^{20} = +17.0°$ C. (c 1, 0.1N hydrochloric acid)
Ultraviolet absorption spectrum: Terminal absorption only.
Infrared absorption spectrum: (As shown in FIG. 3) Characteristic absorption bands at 3220, 2950, 1720, 1620, 1510, 1260, 1150, 1000, 800 cm$^{-1}$ (KBr disc method).
Elementary analysis: C, 21.12; H, 5.92; N, 8.30; O, 46.27; P, 17.92%.
FD-mass spectrum: m/e 154 (M+ +1)
Silica gel thin layer chromatography: Rf=0.22 (n-butanol:acetic acid:water=2:1:1)
Cellulose thin layer chromatography: Rf=0.43 (ditto)

From the elementary analysis and FD-mass spectrum given above, MP-103 substance is determined to have the molecular formula $C_3H_8NO_4P \cdot H_2O$.

From the physicochemical properties described above, as well as other studies, MP-103 substance is identified to be 2-amino-3-(hydroxy)phosphinoylpropionic acid having the following formula (III):

(III)

MP-104 substance

Appearance: Amorphous powder.

Solubility: Readily soluble in water, hardly soluble in organic solvents such as ethanol, acetone, chloroform and ethyl ether.

Specific rotation: $[\alpha]_D^{20} = -6.5°$ (c 1, 0.1N hydrochloric acid)

Ultraviolet absorption spectrum: Terminal absorption only.

Figure 4:
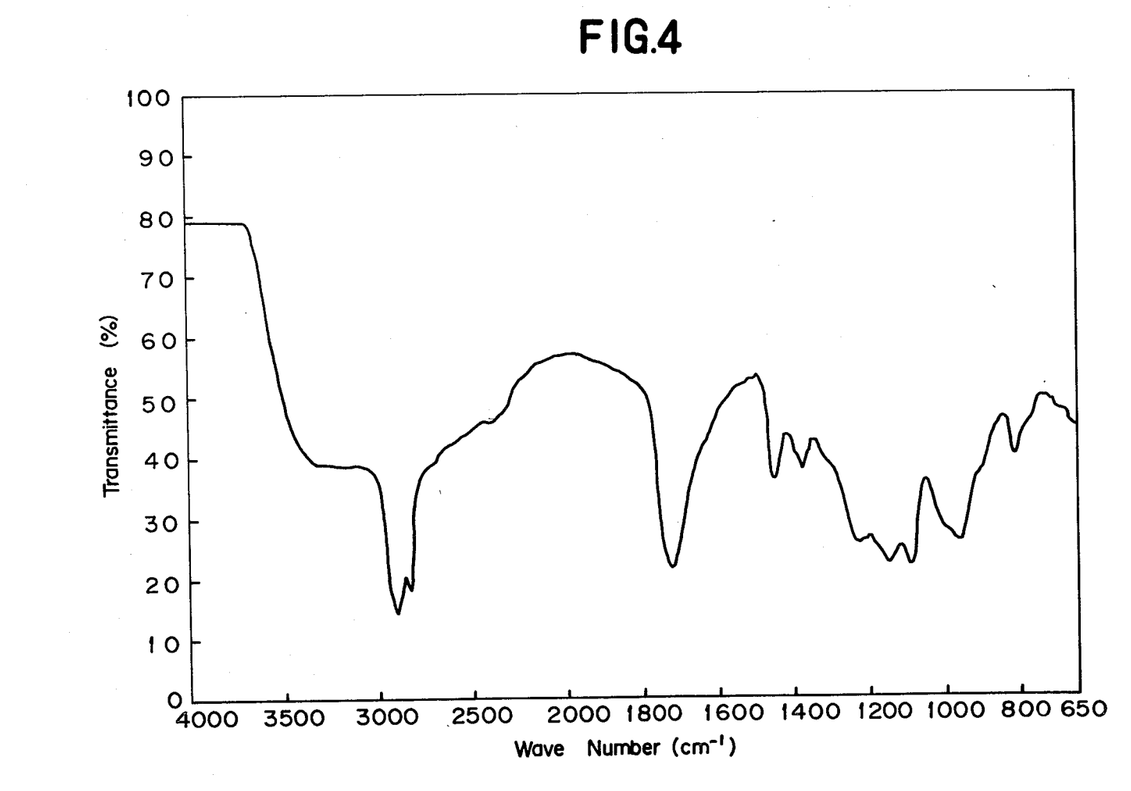

Infrared absorption spectrum: (As shown in FIG. 4) Characteristic absorption bands at 3000~3400, 1720, 1230, 1150, 1090, 960, 810 cm$^{-1}$ (measured in Nujol).

Elementary analysis: C, 20.94; H, 4.89; O, 55.73; P, 17.89%.

FD-mass spectrum: m/e: 154 (M+)

Cellulose thin layer chromatography: Rf=0.3 (n-butanol:acetic acid:pyridine:water=4:1:1:1)

From the elementary analysis and the FD-mass spectrum given above, the molecular formula of MP-104 substance is determined to be $C_3H_7O_5P \cdot H_2O$.

From the physicochemical properties described above, as well as other studies, MP-104 substance is identified to be 2-hydroxy-3-(hydroxy)phosphinoylpropionic acid having the following formula (IV):

(IV)

It has been confirmed from extensive studies that the production of SF-1293 substance may be remarkably increased by the addition of MP-101, MP-102, MP-103 and/or MP-104 substances upon the cultivation of the aforesaid SF-1293 substance-producing microorganisms. Thus, MP-101, MP-102, MP-103 and MP-104 substances turned out very important precursors of the useful herbicide SF-1293 substance.

It has been also confirmed that MP-101 and MP-102 substances are useful as the intermediates for synthesis of a herbicide 2-amino-4-(hydroxy) (methyl)phosphinoylbutyric acid (disclosed in Japanese Laid-Open Patent Application No. 92628/1979, U.S. Pat. No. 4,265,654, etc.) and for synthesis of the aforesaid herbicide SF-1293 substance. Chemical conversion of MP-101 and MP-102 substances to 2-amino-4-(hydroxy) (methyl)phosphinoylbutyric acid and SF-1293 substance is performed according to the processes described below:

Process 1

(V)

(VI)

(VII)

(wherein $R^1$ is an amino-protecting group, and $R^2$ is a carboxy- or phosphynyl-protecting group)

Process 2

(VIII)

(IX)

(X)

(wherein $R^1$ is an amino-protecting group, and $R^2$ is a carboxy- or phosphinyl-protecting group).

Namely, Compounds (V) and (VIII) derived from MP-101 and MP-102 substances, respectively, are reacted with methyl iodide or methyl bromide in an organic solvent such as benzene, toluene, xylene or N,N-dimethylformamide in the presence of a base such as metallic sodium, sodium hydride or lithium isopropylamide to give Compounds (VI) and (IX), respectively, in which a methyl group is introduced to the phosphynyl moiety. The reaction is performed at 50° to 110° C. over 2 to 6 hours. The base is used at 1 to 1.5 equivalents to the starting material. Methyl iodide or methyl bromide is used at 1 to 5 equivalents to the starting material. Aminoprotecting groups to be employed include, for instance, formyl group, acetyl group, trifluoroacetyl group, benzyloxycarbonyl group, p-methoxybenzyloxycarbonyl group, t-butoxycarbonyl group and tosyl group. Carboxy- and phosphinyl-protecting groups to be employed include, for instance, lower alkyl groups such as methyl, ethyl and t-butyl, benzyl group, p-methoxybenzyl group and benzhydryl group which are protecting groups conventionally employed in peptide synthesis.

By deprotecting the thus obtained intermediates (VI) and (IX) with an acid or alkali, or by means of catalytic reduction, there may be obtained the desired 2-amino-4-(hydroxy) (methyl)phosphinoylbutyric acid (VII) and SF-1293 substance (X), respectively. The reaction will be described in more detail in Referential Examples given herein later.

It has been further confirmed that MP-103 substance shows activity against vaccinia virus and herpes simplex virus (HSV II type) which are DNA virus. Results of anti-cytopathic effect, which is indicative of anti-viral activity, of MP-103 substance are shown in Table 1.

TABLE 1

|  | Vaccinia virus | Herpes simplex virus (HSV II type) |
| --- | --- | --- |
| MP-103 substance 500 μg/ml | 4.80 | 7.50 |
| MP-103 substance 250 μg/ml | 5.30 | 8.10 |
| MP-103 substance 125 μg/ml | 5.30 | 8.50 |
| Control (no addition) | 6.80 | 8.80 |

(Unit: Log(TCID$_{50}$/ml))

This invention will be explained in more detail with reference to the following Examples, Experiment and Referential Examples.

EXAMPLE 1

In 10 ml of a pre-culture medium comprising 2.0% soluble starch, 1.0% polypeptone, 0.3% meat extract and 0.05% dipotassium hydrogenphosphate, adjusted to pH 7.0, a culture of *Streptomyces hygroscopicus* SF-1293 strain was inoculated. Reciprocal shaking culture was continued at 28° C. for 24 hours. At the end of the period, the broth was then transplanted to 80 ml of a culture medium having the same composition, and successively transfer-cultured at 28° C. for 24 hours to give a mother culture for jar fermentation. 4.0 l of a culture medium comprising 4.4% glucose, 2.25% Sun Grain, 3.5% wheat malt and 0.1% potassium dihydrogenphosphate was charged in a jar fermentor, which medium was inoculated with the mother culture, then the cultivation was performed at 28° C., with stirring and aeration.

After cultivation for 144 hours, the culture broth was adjusted to pH 2.0 and the mycelia were removed by centrifugation to give 2.0 l of filtrate. The filtrate was passed into a column containing 300 ml of Dowex 50W×2 (H+ form) and eluted with water. Fractions containing MP-102 substance were then passed into a column containing 200 ml of Dowex 1×2 (CH$_3$COO$^-$ form), washed with water and then eluted with 1N acetic acid. Fractions containing MP-102 substance were concentrated to give crystals, which were collected by filtration to give 2.4 g of MP-102 substance in the form of white crystals.

EXAMPLE 2

Cultivation was performed, with stirring and aeration, under the similar conditions as in Example 1. The culture broth was periodically sampled to determine the production of MP-101 substance with an automatic amino acid analyzer (Model MLC-703, available from Atoh Co., Japan; retention time, 11 minutes), the results of which are shown in the following Table 2.

TABLE 2

| Production of MP-101 Substance | | |
| --- | --- | --- |
| Cultivation Period hrs. | pH | Yield of MP-101 Substance |
| 144 | 6.90 | below 50 (μg/ml) |
| 168 | 7.10 | 150 |
| 192 | 7.40 | 510 |
| 216 | 8.15 | 1,320 |

The culture broth that had been cultivated for 216 hours with stirring and aeration was adjusted to pH 2.0. The mycelia were removed by centrifugation to give 2.0 l of filtrate. The production of MP-101 substance in the filtrate was confirmed to be 1,320 μg/ml by amino acid analysis. The filtrate was then passed into a column containing 300 ml of Dowex 50W×2 (H+ form) and eluted with water. Fractions containing MP-101 substance were passed into a column charged with 200 ml of Dowex 1×2 (CH$_3$COO$^-$ form), washed with water and then eluted with 0.3N acetic acid. Fractions containing MP-101 substance were concentrated to separate white crystals, which were collected by filtration to give 1.13 g of MP-101 substance in the form of white crystals.

EXAMPLE 3

In 10 ml of a pre-culture medium comprising 2.0% soluble starch, 1.0% polypeptone, 0.3% meat extract and 0.05% dipotassium hydrogenphosphate, adjusted to pH 7.0, a culture of *Streptomyces hygroscopicus* MP-103 strain (FERM No. 6328) was inoculated.

Reciprocal shaking culture was continued at 28° C. for 24 hours. At the end of the period, the broth was then placed in 80 ml of a culture medium having the same composition, and successively transfer-cultured at 28° C. for 24 hours to give a mother culture for jar fermentaion, 4.0 l of a culture medium comprising 4.0% glucose, 2.25% Sun Grain, 3.5% wheat malt, 0.1% potassium dihydrogenphosphate and 0.0001% cobalt chloride was charged in a jar fermentor, which medium was inoculated with the mother culture, then the cultivation was performed at 28° C., with stirring and aeration. After cultivation for 144 hours, the culture broth was adjusted to pH 2.0 and the mycelia were removed by centrifugation to give 2.0 l filtrate.

Production in the culture broth of MP-103 substance was determined with an automatic amino acid analyzer (Model MLC-703, available from Atoh Co., Japan; retention time, 11 minutes), showing the value 170 μg/ml. The filtrate was passed into a column containing 450 ml of Dowex 50W×2 (H+ form), eluted with water until the elution of MP-103 substance was in complete. About 1.8 l of the eluate was passed into a column containing 600 ml of Dowex 1×2 (CH$_3$COO$^-$ form), first washed with water then eluted with 0.5N hydrochloric acid. Fractions containing MP-103 substance and MP-104 substance were collected from the eluate, concentrated and the hydrochloric acid was removed. After adding water to make about 30 ml, the concentrate was passed into a column containing 700 ml of Dowex 50W×2 (H+ form), eluted with water to collect fractions in 20 ml portions. Then the fractions that give a single spot (Rf 0.43) with ninhydrin on cellulose thin layer chromatography when developed with n-butanol:acetic acid:water=(2:1:1) were concentrated, affording 180 mg of MP-103 substance in the form of white crystals.

EXAMPLE 4

120 ml of fractions that passed through the column containing 700 ml of Dowex 50W×2 (H+ form) in Example 1 without stopping was concentrated to about 10 ml. The concentrate was passed into a column containing 950 ml of Sephadex G-10, eluted with water to collect fractions in 10 ml portions. Fractions containing MP-104 substance were collected and concentrated. The concentrate was made pasty with cellulose and layered over a column containing 130 ml of cellulose, prepared with n-butanol:acetic acid:water:pyridine=(4:1:1:1), then eluted with an eluent having the same system to collect fractions in 7.5 ml portions. Fractions containing MP-104 substance were collected, concentrated and passed through a column charged with 5 ml of Dowex 50W×2 (H+ form), then again concentrated to give 110 mg of MP-104 substance in the form of a pale yellow powder.

EXPERIMENT 1

In 10 ml of a pre-culture medium comprising 2.0% soluble starch, 1.0% polypeptone, 0.3% meat extract and 0.05% dipotassium hydrogenphosphate, adjusted to pH 7.0, a culture of *Streptomyces hygroscopicus SF-1293* strain (FERM No. 996) was inoculated. Reciprocal shaking culture was continued at 28° C. for 24 hours. The seed culture was then transplanted to a culture medium, at the rate of 2%, comprising 3.9% glycerin, 3.6% wheat malt, 0.5% Sun Grain, 0.1% potassium dihydrogenphosphate and 0.0001% cobalt chloride, then the cultivation was performed at 28° C. for 7 days. During the cultivation, the precursors MP-101, MP-102, MP-103 and MP-104 substances were added to the culture broth at the concentration and time as shown in Table 3. When the cultivation was in complete, the culture broth was made acidic, centrifuged to obtain a supernatent, which was then subjected to amino acid analysis with an automatic amino acid analyzer (Model MLC-703, Atoh Co., Japan; retention time, 14 minutes) to determine the production of SF-1293 substance in the culture broth. The results are shown in Table 3.

TABLE 3

| Substance added | Concentration | Time of addition | Potency of SF-1293 production (μg/ml) |
| --- | --- | --- | --- |
| MP-101 substance | 300 μg/ml | 3rd day | 480 |
|  | 300 μg/ml | 3rd, 4th and 5th days, each 100 μg/ml | 610 |
| MP-102 substance | 500 μg/ml | 3rd day | 700 |
|  | 500 μg/ml | 1st, 2nd, 3rd, 4th and 5th days, each 100 μg/ml | 790 |
| MP-103 substance | 300 μg/ml | 3rd day | 650 |
|  | 300 μg/ml | 3rd, 4th and 5th days, each 100 μg/ml | 820 |
| MP-104 substance | 300 μg/ml | 3rd day | 505 |
|  | 300 μg/ml | 3rd, 4th and 5th days, each 100 μg/ml | 590 |
| Control (No addition) |  |  | 410 |

It is seen from the above Table 3, that the production rate of SF-1293 substance may be raised by the addition of MP-101, MP-102, MP-103 or MP-104 substance.

Referential Example 1

610 mg of MP-101 substance was suspended in 20 ml of water, and the suspension was adjusted to pH 7.5 with 1N sodium hydroxide. 1,300 mg of di-t-butyl dicarbonate was added to the suspension, and the mixture was stirred at room temperature for 7 hours to complete the reaction, while maintaining pH at 7.5~8.0. The reaction mixture was extracted with 20 ml of ethylacetate to remove the excess reactants, and the aqueous layer was adjusted to pH 2.0 with 2N hydrochloric acid under cooling, then lyophilized.

The residue was extracted with 30 ml of acetone and an ethereal solution of diazomethane was added to the solution, which was allowed to stand at 10° C. for 2 hours. The reaction mixture was evaporated to dryness, affording 810 mg of 2-t-butoxycarbonylamino-4-(methoxy)phosphinoyl-butyric acid methyl ester in the form of an oil.

Elementary analysis:

Calculated for $C_{11}H_{22}NO_6P$: C, 44.75; H, 7.46; N, 4.75; O, 32.54; P, 10.51%.

Found: C, 44.53; H, 7.58; N, 4.17; P, 9.76%.

NMR (CDCl$_3$) δppm: 1.47 (9H, s, —COOC(CH$_3$)$_3$), 1.7~2.2 (4H, m, H$_3$, H$_4$), 3.78 (3H, s, —COOCH$_3$), 3.80 (3H, d, J=11 Hz, P-OCH$_3$), 7.1 (1H, d, J=536 Hz, P-H).

400 mg of the product thus obtained was dissolved in 6 ml of toluene and 34 mg of sodium hydride was added, then the mixture was stirred at room temperature for 30 minutes, followed by further stirring at 70° C. for 1 hour.

400 mg of methyl iodide was added, and the mixture was vigorously stirred at 60°~70° C. for 3 hours. After allowing to cool, the reaction mixture was neutralized with acetic acid, then concentrated under reduced pressure. The residue was dissolved in 6 ml of 3N hydrochloric acid and hydrolyzed at 70° C. for 2 hours. The reaction mixture was evaporated to dryness, dissolved in 5 ml of water and adjusted to pH 2.5 with 3N sodium hydroxide. The solution was passed into a column containing 30 ml of Dowex 1×2 (AC form) and eluted with 0.5N acetic acid. Fractions containing the desired product was concentrated and crystallized with water/ethanol to give 130 mg of 2-amino-4-(hydroxy)-(methyl)-phosphinoylbutyric acid in the form of white crystals.

Referential Example 2

620 mg of MP-102 substance was suspended in 30 ml of water, and the suspension was adjusted to pH 8 with 1N sodium hydroxide. 600 mg of di-t-butyl dicarbonate was added to the suspension, and the mixture was stirred at room temperature for 5 hours to complete the reaction while maintaining pH at 8. The reaction mixture was washed with 30 ml of ethyl acetate to remove the excess reactants, and the aqueous layer was adjusted to pH 2, then extracted twice with 30 ml of a mixture of n-butanol:ethyl acetate (1:3). The extract was concentrated under reduced pressure and the residue was dissolved in 5 ml of methanol. An ethereal solution of diazomethane was added to the solution, which was then allowed to stand at 15° C. for 3 hours. The reaction mixture was concentrated to dryness, giving 780 mg of 2-t-butoxycarbonylamino-4-(methoxy)phosphinoylbutyryl-L-alanyl-L-alanine methyl ester in the form of a white powder.

Elementary analysis:
Calculated for $C_{17}H_{32}N_3O_8P$: C, 46.68; H, 7.32; N, 9.61; O, 29.29; P, 7.09%.
Found: C, 46.23; H, 7.46; N, 9.35; P, 6.92%.
NMR ($CDCl_3$) δppm: 1.45 (9H, s, $-COO(CH_3)_3$), 1.6~2.2 (4H, m, $H_3$, $H_4$), 3.73 (3H, s, $-COOCH_3$), 3.82 (3H, d, J=11.2 Hz, P-O$CH_3$), 7.2 (1H, d, J=538 Hz, P-$H$).

440 mg of the product thus obtained was dissolved in 5 ml of N,N-dimethylformamide and 30 mg of sodium hydride was added. The mixture was stirred first at room temperature for 40 minutes, then at 60° C. for 2 hours. 700 mg of methyl iodide was added to the mixture, which was then vigorously stirred at 50°~60° C. for 2 hours.

After allowing to cool, the reaction mixture was neutralized with acetic acid and concentrated under reduced pressure. The residue was dissolved in 5 ml of acetonitrile, then 600 mg of trimethylsilyl iodide was added to the solution, which was stirred at 50° C. for 2 hours, then concentrated to dryness under reduced pressure. The residue was dissolved in 5 ml of trifluoroacetic acid, and the solution was allowed to stand at room temperature for 1 hour. The solution was again concentrated to dryness and the residue was dissolved in 5 ml of water, which solution was adjusted to pH 2 with 3N sodium hydroxide. The solution was passed into a column containing 40 ml of Dowex 1×2 (AC form), eluted with 0.3N acetic acid. Fractions containing the desired product were concentrated to give 153 mg of SF-1293 substance.

Referential Example 3

600 mg of MP-101 substance was suspended in 30 ml of methanol, then an equimolar amount of pyridine was added to solubilize the substance. 2 ml of methyl trifluoroacetate was added to the solution, which was then stirred at room temperature for 15 hours, while maintaining the mixture at slightly alkaline condition by addition of pyridine. The reaction mixture was concentrated to dryness and the residue was dissolved in 5 ml of water, adjusted to pH 2 with 2N hydrochloric acid and lyophilized. The residue was extracted with 25 ml of acetone and an ethereal solution of diazomethane was added to the extract, which was then allowed to stand at 15° C. for 3 hours. The reaction mixture was concentrated to dryness and the residue was dissolved in 30 ml of ethyl acetate. The solution was washed with 10 ml of water and the ethyl acetate layer was concentrated to give 790 mg of 2-trifluoroacetylamino-4-(methyl)phosphinoylbutanoic acid methyl ester in the form of an oil.

Elementary analysis:
Calculated for $C_8H_{13}NO_5PF_3$: C, 32.99; H, 4.47; N, 4.81; O, 27.49; P, 10.65%.
Found: C, 32.75; H, 4.53; H, 4.67; P, 9.23%.
NMR ($CDCl_3$) δppm: 1.65~2.3 (4H, m, $H_3$, $H_4$), 3.76 (3H, s, $-COOCH_3$), 3.81 (3H, d, J=11 Hz, P-O$CH_3$), 7.08 (1H, d, J=540 Hz, P-H).

360 mg of the product was treated in the similar manner as in Example 1 to afford 83 mg of 2-amino-4-(hydroxy)-(methyl)phosphinoylbutanoic acid in the form of white crystals.

We claim:

1. Compounds represented by the following formula:

wherein n is an integer of 1 or 2; $R^1$ is an amino group when n is 2, or an animo group or a hydroxyl group when n is 1; and $R^2$ is a hydroxyl group.

2. The compound according to claim 1, having the following formula:

wherein R is a hydroxyl group.

3. The compounds according to claim 1, having the following formula:

wherein R is an amino group or a hydroxyl group.

4. The compound according to claim 3, which is 2-amino-3-(hydroxy)phosphinoylpropionic acid.

5. The compound according to claim 3, which is 2-hydroxy-3-(hydroxy)phosphinoylpropionic acid.

* * * * *